United States Patent [19]

Münnich et al.

[11] 4,253,326
[45] Mar. 3, 1981

[54] APPARATUS FOR DETERMINING THE PROPERTIES OF A LUBRICANT

[75] Inventors: Hermann Münnich, Bad Kissingen; Hermann Glöckner, Schweinfurt, both of Fed. Rep. of Germany

[73] Assignee: SKF Kugellagerfabriken GmbH, Schweinfurt, Fed. Rep. of Germany

[21] Appl. No.: 56,650

[22] Filed: Jul. 11, 1979

[30] Foreign Application Priority Data

Jul. 15, 1978 [DE] Fed. Rep. of Germany ....... 2831158

[51] Int. Cl.³ ............................................... G01N 3/56
[52] U.S. Cl. ............................................... 73/10
[58] Field of Search ............................ 73/10, 64, 59; 23/230 HC

[56] References Cited

U.S. PATENT DOCUMENTS

| | | | |
|---|---|---|---|
| 2,108,580 | 2/1938 | Drake et al. | 73/64 X |
| 3,785,196 | 1/1974 | Smith | 73/64 |
| 3,823,599 | 7/1974 | Litz et al. | 73/10 |

Primary Examiner—Jerry W. Myracle
Attorney, Agent, or Firm—Eugene E. Renz, Jr.

[57] ABSTRACT

Apparatus for determining the properties of lubricants which is of comparatively simplified construction and is capable of analyzing the properties of a lubricant in a relatively short period of time with a relatively small quantity of lubricant in a highly accurate manner. The apparatus comprises an axial cylindrical roller bearing supported on the frame of the apparatus by a hydrostatic cushion. The apparatus includes a disc member which supports the housing disc of the axial cylindrical roller bearing which is engaged by a leaf spring equipped with a resistant strain gauge for measuring the moment of friction. A bell-shaped top lies on the spindle disc of the axial cylindrical roller bearing and is rotated by motor with an infinitely variable drive to which a tachometer is connected by a distance gauge arranged between the disc member and the bell-shaped top which measures a change in the distance of the contact surface of the axial cylindrical roller bearings and consequently the lubricant film thickness. The apparatus includes, in the present instance, two recorders for converting the measuring impulses of the moment of friction, the distance of the contact surfaces of the axial cylindrical roller bearing and the rotational speed to provide curves of the moment of friction as a function of speed and the lubricating film thickness as a function of speed.

5 Claims, 3 Drawing Figures

APPARATUS FOR DETERMINING THE PROPERTIES OF A LUBRICANT

BACKGROUND OF THE INVENTION

The present invention relates to apparatus for determining the properties of a lubricant and specifically to one which is of relatively simplified construction wherein the film-forming properties of a comparatively small amount of lubricant with roller contact can be determined quickly and without sizeable operating and monitoring equipment. The test apparatus of the present invention is characterized by novel features of construction and arrangement wherein the extraneous forces attributable to the measurement apparatus masking the true properties of a lubricant under evaluation are negligible and thus the evaluation is highly accurate.

There are presently test machines for lubricants which permit examination of the behavior of machine parts moving against each other under high loads.

A suitable lubricant for a given roller bearing is determined by considering the elasto-hydrodynamic theory of lubrication, commonly called the EHD theory. The pressure dependency of viscosity considering the very complicated pressure and temperature phenomenon in the lubrication gap has a decided effect on friction and wear. The magnitude of lubricant characteristics such as viscosity as a function of pressure and temperature, shape of the lubricating gap (lubricating film thickness) and others cannot be easily detected as to their individual effect.

In these known test devices, the sliding or rolling friction of bodies moving relative to one another is examined whereby the bodies are either moved against each other in one direction or actuated to effect an oscillating movement. A known test machine of this type is the so-called two-disc test bench wherein friction for certain operating conditions can be measured quickly and accurately. In this unit, two cylindrical discs contact each other at the periphery and are both driven independently of each other with an infinitely variable adjustment. The frictional force at the contact area produces a parallel displacement of the upper test disc together with its support bearing since the support bearing is hinged with only two leaf springs to the test bench frame. The frictional force acts against a force measuring strip and is measured with strain gauges. The contact pressure between the discs is applied by calibrated springs. The number of disc revolutions is then recorded with a photo cell and indicated on an electronic counter. Simultaneously with the friction measurement, the lubrication condition is constantly checked by measuring the current transfer at the location of contact. The individual current transfers during contact of roughness peaks and their distribution over the periphery are indicated on a cathode ray oscillograph. This apparatus and procedure are set forth in a German publication entitled "Konstruktion", 23rd Edition dated July, 1971 starting at Page 245.

There are also prior known test apparatus wherein the effects of dynamic forces on the bearing surfaces can be examined, such as the effect of vibrations. During a test on lubricants, the operating temperature, the time span for certain damage, the surfaces of elements moved against each other, more commonly known as wear and the co-efficient of friction are measured. After running the tests the appearance of the running marks in the contacting bodies such as rolling elements is evaluated.

In another known device for determining the lubricating properties of a liquid, the lubricant is applied to a rotating plate to form a film and a sensor is brought into contact with the rotating plate to measure the elapsed time to the breakdown of the lubricant as the result of frictional heat. A sensor is arranged at the free end of an elastic arm fastened to a pivotally mounted frame which is moveable in the plane of the plate by reason of its elasticity. Additionally, indicating means are provided for detecting the angular movement of the sensor at the moment of breakdown of the liquid film. This system is illustrated in German Pat. No. 2,034,812.

Even though these prior known apparatus are generally suitable for the purposes intended, they have a number of deficiencies and drawbacks. For example, tedious and time consuming investigations involving large amounts of lubricant are required in order to obtain relatively accurate results or statements concerning the film forming properties of the lubricant. For this reason it is usually necessary to employ several apparatus and this requires a relatively sizeable operating and monitoring effort.

With the foregoing in mind, it is an object of the present invention to provide a simple apparatus wherein the film forming properties of the lubricant with roller contact can be determined quickly and without sizeable operating and monitoring effort with a comparatively small quantity of lubricant. For example, the film forming properties of a lubricant can be determined with test apparatus in accordance with the present invention in a maximum time of 30 seconds and with as little as two grams of lubricant. It is also possible to intentionally "construct" lubricants with the test results gained.

The test apparatus of the present invention incorporates an axial cylindrical roller bearing whereby shape and surface tolerances of the bearing parts are attained which prevent harmful effects on the test results. By supporting an axial cylindrical roller bearing on a hydrostatic cushion with extremely low friction, a measurement of the moment of friction is possible in the simplest way via force pickups to which resistance strain gauges are attached by adhesion.

In order to center the bearing discs of the axial cylindrical roller bearing accurately relative to one another, a radial rolling bearing, in the present instance a ball bearing, is provided as a floating bearing between these two parts. Distance changes of the two bearing discs of the axial cylindrical roller bearing are measured by a capacitive transmitter. This capacitive transmitter measuring means measures film thickness at the center of rotation and is therefore highly tolerant of deviations in the geometry of the test bearing in the connecting parts resulting in highly accurate measuring values.

By reason of the arrangement of the capacitive transmitter in the trunnion-like shoulder surrounded by the bell-shaped top, an "air bubble" is formed so that even when running a test with a large amount of lubricant in the area of the capacitive transmitter and its reference surface the measuring result of the transmitter is not negatively affected by the lubricant. More specifically, by reason of the fact that the capacitive transmitter measuring means is located at the center of rotation, the centripetal force effect tends to keep lubricant out of this region thus providing another insurance against negatively effecting measuring values.

BRIEF DESCRIPTION OF THE DRAWINGS

These and other objects of the present invention and the various features and details of the operation and construction of apparatus in accordance with the present invention is hereinafter more fully set forth with reference to the accompanying drawings wherein.

DESCRIPTION OF A PREFERRED EMBODIMENT

Figure 1:
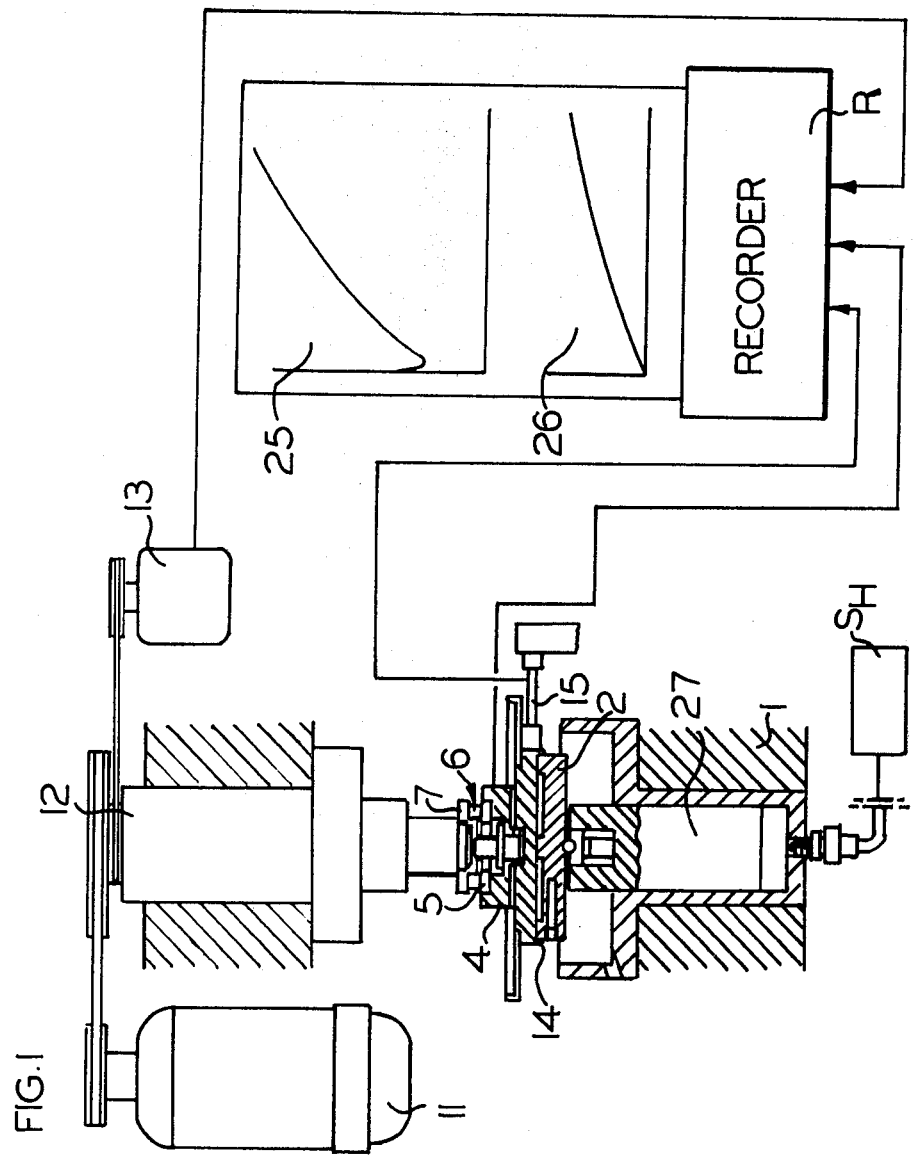
FIG. 1 is a schematic illustration of a test apparatus in accordance with the present invention.
Figure 2:
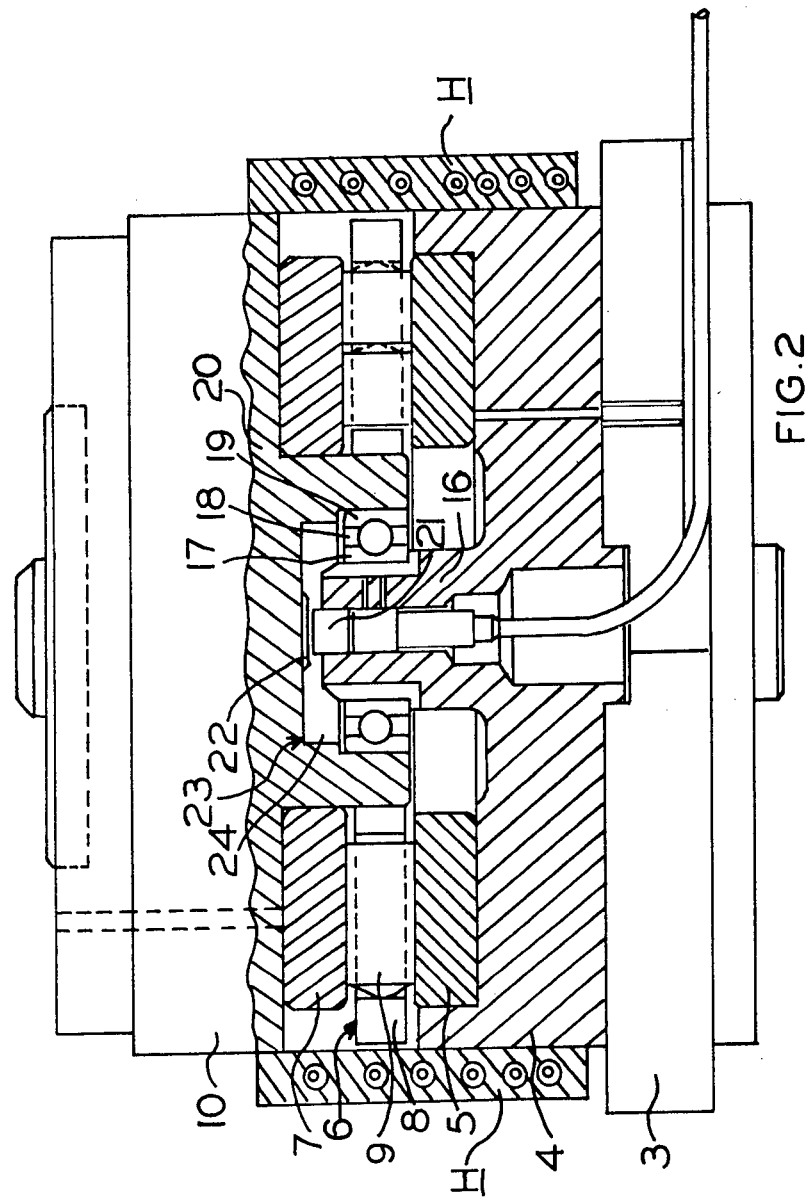
FIG. 2 is an enlarged partial view of the test apparatus of the present invention.
Figure 3:
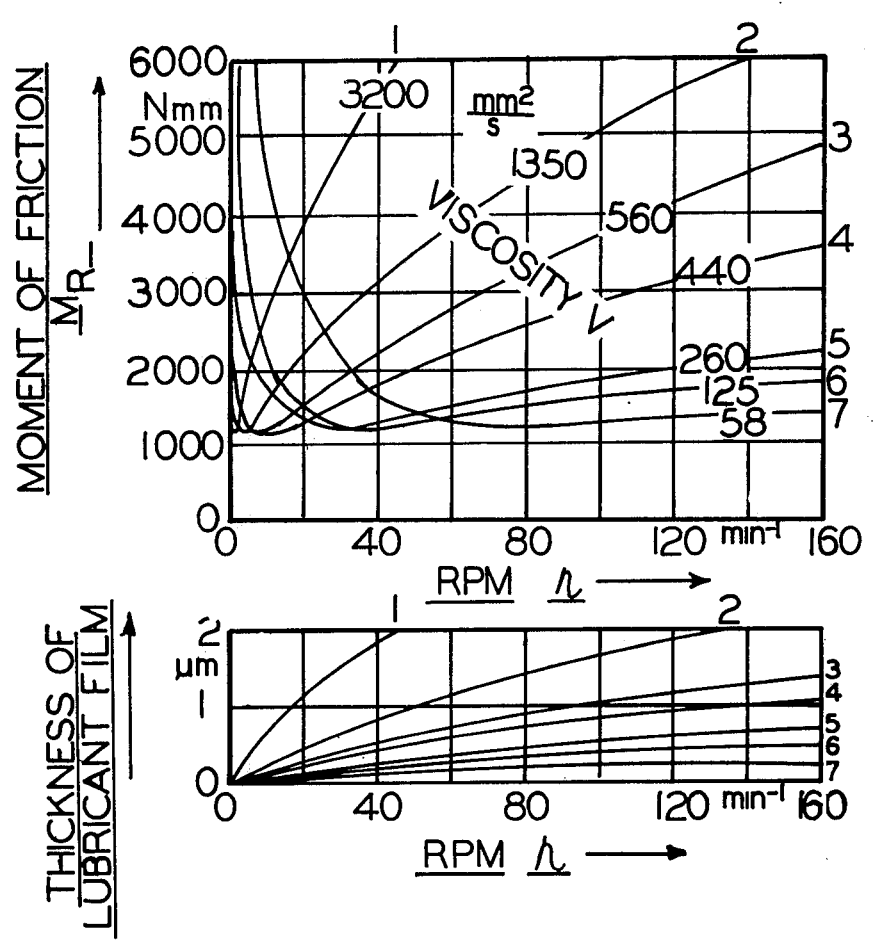
FIG. 3 shows values for various lubricants with different viscosities as determined by the test apparatus of the present invention.

Referring now to the drawings and particularly to FIG. 1 thereof, the basic elements of the test apparatus of the present invention which are shown schematically comprise a machine frame 1, a hydrostatic axial bearing 2 mounted on the frame which supports a disc 4 via an insulation disc 3 on which the housing disc 5 of an axial cylindrical roller bearing 6 is supported. The bearing 6 also includes a plurality of cylindrical rollers 9 located in the annular space between the housing disc 5 and spindle disc 7 which are spaced and distributed around the periphery in a cage 8 between the bearing discs 5 and 7. The spindle disc 7 confronts and butts up to a bell-shaped top 10 which in turn is supported on a spindle 12 rotated by an infinitely variable drive motor 11. A tachometer 13 engaged by the spindle 12 measures the appropriate number of revolutions of the bearing and transmits this to a conventional recorder R as for example, an optical or magnetic pick up. A leaf spring 15 equipped with resistant strain gauges engages the periphery of disc 14 of the hydrostatic axial bearing 2. These resistant strain gauges are connected in a conventional manner to the recorder R. The disc 4 which carries the housing disc 5 of the axial bearing 6 has a centrally located shoulder 16 forming a trunnion which mounts the inner ring 17 of a radial rolling bearing 18, in the present instance a ball bearing. The outer ring 19 of the bearing supported in the bore of an annular shoulder 20 of the bell-shaped top carries the spindle disc 7 of the axial roller bearing 6. The disc 4 and the bell-shaped top 10 as well as the contacting bearing discs 5 and 7 are accurately centered in this manner relative to one another. One of the bearing rings 17 and 19 of the radial rolling bearing 18 is arranged with a loose fit in or on its seating surface so that the disc 4 may be freely displaced axially in relation to the bell-shaped top 10.

A reference surface 22 for the transmitter 21 is formed in the bottom face 23 of the recess 24 by the annular shoulder 20 of the bell-shaped top 10. The capacitive distance transmitter 21 is also connected with a recorder R. This recorder R is designed in such a way that it receives the impulses sent by the tachometer, impulses from the resistance strain gauges 15 and the capacitive distance transmitter 21. The output of the recorder is used to construct two curves, a curve 25 representing the moment of friction MR as a function of speed (rpm) and a curve 26 of the change in distance of the bearing discs 5 and 7 relative to one another which stated another way is the lubrication film thickness in $\mu$m as a function of speed (rpm). It is noted that when operating the device, there are two lubrication films created, one between the cylindrical rollers and the spindle disc 7 and one between the cylindrical rollers and the housing disc 5. Accordingly, the capacitive transmitter 21 measures a displacement which is twice the lubricant thickness. The hydrostatic axial bearing 2 is supported by a piston 27 via which the load is applied on the axial cylindrical roller bearing 6 by means of a pressure fluid such as oil.

A lubricant is tested in the test apparatus of the present invention in the following manner. The axial cylindrical roller bearing 6 is wetted or filled with the lubricant to be tested. The motor 11 is then operated and the number of revolutions is turned up continuously under a constant load from zero to a predetermined value. After several revolutions of the bearing the lubricant distributes uniformly on the bearing discs and the outside surfaces of the cylindrical rollers 9. Simultaneously the curves 25 and 26 representing the moment of friction and the lubricant film are transcribed in relation to the rpm's. The thickness of the lubricant film increases with speed. The characteristics of the moment of friction is the result of the elasto-hydrodynamic losses which increase with speed, of the friction losses which drop with the speed increase and of the losses in the roller gap which are not dependent on the speed and which are composed of shear and hysteresis losses of the lubricant and of the materials of construction.

Evaluation of the test results with oil-lubricated axial cylinder roller bearings: the film thickness (h) of an oil-lubricated axial cylinder roller bearing can be calculated in a simplified way according to Dowson:

$$h = c \times a^{0.6} \times \eta^{0.7} \times n^{0.7},$$

in which, n (rpm) is the bearing speed; $\eta(N \times s)/m^2$ is the dynamic viscosity and $a(m^2)/(N)$ is the pressure-viscosity coefficient.

The film build up properties of an unknown lubricant can be determined from a comparison of its lubricating film thickness-speed characteristics with the corresponding characteristics of known lubricants. This comparison presents information about its "comparable" viscosity in the Hertzian contact. By using the same axial cylindrical roller bearing in these tests, the ratio $h/n^{0.7}$ can be used to compare the different lubricants.

The elasto-hydrodynamic friction losses in the Hertzian contact depend on the lubricating film thickness. On this basis, a comparison of the moment of friction of an unknown lubricant with the moment of friction of a known lubricant presents additional information about the suitability of the lubricant to build up a lubricating film. This comparison is made with the portion or the branch of the friction characteristics curve which lies to the right of the minimum. The dependency of the lubricating film thickness and the moment of friction on the bearing speed can only be observed when the Hertzian contact surfaces are lubricated with an adequate volume of lubricating oil to build up the size of the lubricating film predicted by elasto-hydrodynamic lubricant theory. An increase in the lubricating film as the result of too much oil commonly described as "squeezing" cannot be observed within the examined speed ranges. However, when the oil volume spread over the bearing discs is not adequate to produce a complete distribution, starvation sets in above a certain speed limit. In this range of partial lubrication the film thickness and the moment of friction are practically independent of the speed.

The film forming properties of the lubricant can be determined quickly and simply with the present invention utilizing a comparatively small amount of lubricant. Therefore, it is also possible to intentionally construct a lubricant with very specific properties especially suitable for a certain application.

Even though the test apparatus of the present invention has been illustrated and described in connection with evaluating lubricants of a given viscosity and under a given load to measure the effect of frictional moment and film thickness as a function of speed, the invention may be utilized to develop other parametric values for a lubricant. For example, it is possible to provide a heating element, in the form of a coil H surrounding the disc 4, to determine the temperature dependency of properties of the lubricant. Other heating means are possible. For example, the entire apparatus may be put into an oven. It is also possible to use a hot air stream directed to the axial cylindrical roller bearing. In this case, the temperature can be detected via suitable measuring device and optionally be recorded by means of a recorder. In this manner, a family of curves can be developed for a lubricant with a given viscosity at a given load which measures the effect of frictional moment and film thickness as a function of temperature.

The load applied to piston 27 of the hydrostatic bearing may be controlled by suitable conventional hydraulic system shown schematically $S_H$ to apply a constant or time varying (vibratory) pressure or load. Thus, it is possible to vary the axial load applied on the axial roller bearing through the hydrostatic bearing and record them by means of an appropriate measuring and recording system and in this manner develop a family of curves measuring the effect of frictional moment and film thickness as a function of load. A family of curves for vibrational frequencies may be developed when the test apparatus is set up to apply vibratory loads.

We claim an:

1. Apparatus for determining the properties of a lubricant comprising an axial cylindrical roller bearing consisting of an axially spaced spindle and housing discs and a plurality of rollers in the annular space between the discs into which the lubricant to be tested is introduced, an annular member which supports the housing disc of the axial cylindrical roller bearing supported on a machine frame by means of a hydrostatic bearing cushion, means for measuring the moment of friction, a bell-shaped top which lies on and confronts the spindle disc, means for rotating the bell-shaped top, means for measuring the rotational speed of the bell-shaped top and the spindle disc, means for measuring the change in distance of the contact surfaces of the axial cylindrical rolling elements and consequently the lubricating film thickness and recording means for converting the measuring impulses of the moment of friction, the distance of the contact surface of the axial cylindrical rolling elements and the speed to provide curves of the moment of friction as a function of speed and the lubricating film thickness as a function of speed.

2. Apparatus as claimed in claim 1 including a radial roller bearing arranged as a floating bearing between the annular disc member and the bell-shaped top for centering the same, one of the rings of the radial bearing supporting one of the bearing discs of the axial cylindrical roller bearing.

3. Apparatus as claimed in claim 2 wherein the annular disc member includes a trunnion-like shoulder to receive the inner ring of the radial roller bearing, the bell-shaped top having an annular shoulder to receive the outer ring of the radial roller bearing.

4. Apparatus as claimed in claim 1 wherein the means for measuring the film thickness is a capacitive transmitter.

5. Apparatus as claimed in claim 4 wherein the capacitive transmitter is arranged at the free end of the trunnion-like shoulder of the annular disc member and including a reference surface in the bottom of the recess formed by the annular shoulder of the bell-shaped top.

* * * * *